United States Patent
Gooch et al.

(10) Patent No.: US 8,748,119 B2
(45) Date of Patent: *Jun. 10, 2014

(54) METHODS FOR DETERMINING CALCINEURIN ACTIVITY, AND USES IN PREDICTING THERAPEUTIC OUTCOMES

(71) Applicant: Emory University, Atlanta, GA (US)

(72) Inventors: Jennifer L. Gooch, Lilburn, GA (US); Brian R. Roberts, Sandy Springs, GA (US); Jan Pohl, Tucker, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/706,750

(22) Filed: Dec. 6, 2012

(65) Prior Publication Data

US 2013/0122514 A1 May 16, 2013

Related U.S. Application Data

(63) Continuation of application No. 12/669,665, filed as application No. PCT/US2008/071726 on Jul. 31, 2008, now abandoned.

(60) Provisional application No. 60/962,884, filed on Aug. 1, 2007.

(51) Int. Cl.
*C12Q 1/42* (2006.01)

(52) U.S. Cl.
USPC .......................................................... 435/21

(58) Field of Classification Search
USPC .......................................................... 435/21
See application file for complete search history.

(56) References Cited

U.S. PATENT DOCUMENTS

| | | | |
|---|---|---|---|
| 6,057,333 A | 5/2000 | Gunaskera et al. | |
| 6,569,867 B2 | 5/2003 | Chu et al. | |
| 6,605,593 B1 | 8/2003 | Naicker et al. | |
| 6,613,739 B1 | 9/2003 | Naicker et al. | |
| 6,624,302 B2 | 9/2003 | Chu et al. | |
| 6,784,156 B2 | 8/2004 | Or et al. | |
| 6,809,077 B2 | 10/2004 | Or et al. | |
| 6,875,581 B1 | 4/2005 | Voelkel | |
| 6,979,671 B2 | 12/2005 | Or et al. | |
| 7,012,064 B2 | 3/2006 | Or et al. | |
| 7,012,065 B2 | 3/2006 | Or et al. | |
| 2003/0045679 A1 | 3/2003 | Crawford | |
| 2005/0074438 A1 | 4/2005 | Kim et al. | |
| 2007/0190588 A1 | 8/2007 | Ornatsky | |
| 2010/0159475 A1* | 6/2010 | Tumlin et al. | 435/7.1 |
| 2013/0059314 A1* | 3/2013 | Gooch et al. | 435/7.4 |

FOREIGN PATENT DOCUMENTS

| | | |
|---|---|---|
| WO | 9612806 | 5/1996 |
| WO | WO2007022074 A2 | 2/2007 |
| WO | 2009141121 | 11/2009 |

OTHER PUBLICATIONS

Roberts B. et al. A Fluorimetric Method for Determination of Calcineurin Activity. Cell Calcium 43(5)515-519, 2008.*
Supplemental European Search Report dated Oct. 28, 2010.
Enz, at al., "Nonradioactive Assay for Protein Phosphatase 2B (Calcineurin) Activity Using a Partial Sequence of the Subunit of cAMP-Dependent Protein Kinase as Substrate," Analytical Biochemistry 216, pp. 147-153 (1994).
Roberts, et al., "A Fluorimetric Method for Determination of Calcineurin Activity, " Cell Calcium 43 (2008) pp. 515-519.
Biomol Green Calcineurin Assay Kit: Catalog No. AK-816.
Calbiochem Calcineurin Assay Kit: Catalog No. 207005.
Calbiochem Calcineurin Assay Kit: Catalog No. 207007.
Enzo Biomol Calcineurin Assay Kit: Catalog No. AK-804.
Fruman et al., 1996, Measurement of calcineurin phosphatase activity in cell extracts, Method EnzymoL. 9: pp. 146-154.
Gooch et al., 2001, Insulin-like growth Factor induces renal cell hypertrophy via a calcineurin-dependent mechanism, J. BioL Chem. 276 : pp. 42492-42500.
Gooch et al., 2004, Involvement of calcineurin in transforming growth factor-beta-mediated regulation of extracellular matrix accumulation, J. BioL Chem. 279: pp. 15561-15570.
Gooch et al., Calcineurin A-alpha but not A-beta is required for normal kidney development and function, Am. J. Pathol. 165: pp. 1755-1765.
Gooch et al., 2004, Calcineurin is activated in diabetes and is required for glomerular hypertrophy and ECM accumulation, Am. J. Physiol. Renal. Physiol. 284 : F144-FI54.
Koefoed-Nielsen, P.B., et al., 2004, Validation of the Calcineurin Phosphatase Assay. Clinical Chemistry, 50: pp. 2331-2337.
Kupcho et al., 2004 A Homogeneous, Nonradioactive, High-Throughput Fluorogenic Protein Phosphatase Assay. Journal of Biomolecular Screening, 9: pp. 223-231.
Kuroda et al., 2004 Phosphopeptide-selective column-switching RP-HPLC with a titania precolumn, AnaL Sci. 20: pp. 1313-1319.
Pinkse et al., 2004, Selective isolation at the femtomole level of phosphopeptides from proteolytic digests using 20-NanoLC-ESI-MS/MS and titanium oxide precolumns, Anal. Chem. 76: pp. 3935-3943.
Sellar et al., 2006, Spectrophotometric assay for calcineurin activity in leukocytes isolated from human blood. Analytical Biochemistry, 358: pp. 104-110.
Promega 2009, ProFluor Ser/Thr PPas Assay Technical Bulletin Part #TB324.

* cited by examiner

*Primary Examiner* — Ralph Gitomer
(74) *Attorney, Agent, or Firm* — Emory Patent Group; James C. Mason; Susanne Hollinger

(57) ABSTRACT

One aspect of the present disclosure encompasses methods for determining a protein kinase or phosphatase activity in a biological sample, comprising: contacting in a reaction mix a first test sample and a fluorescently-labeled peptide substrate capable of being modified by a protein phosphatase or a protein kinase, contacting the reaction mix with a $TiO_2$ matrix, thereby partitioning fluorescently-labeled phosphorylated peptide from fluorescently-labeled dephosphorylated peptide; and determining the fluorescence of the fluorescently-labeled dephosphorylated peptide, thereby determining a protein kinase or phosphatase activity.

10 Claims, 10 Drawing Sheets

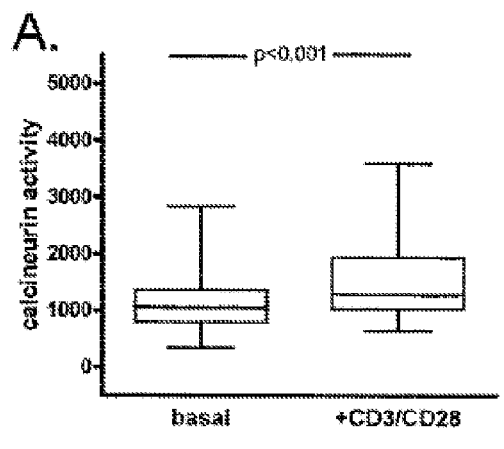
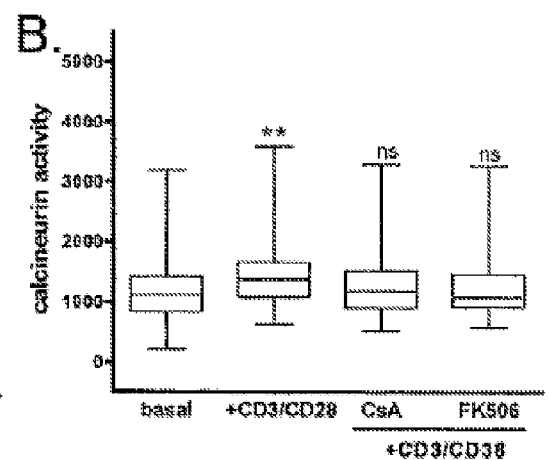
FIG. 5A            FIG. 5B
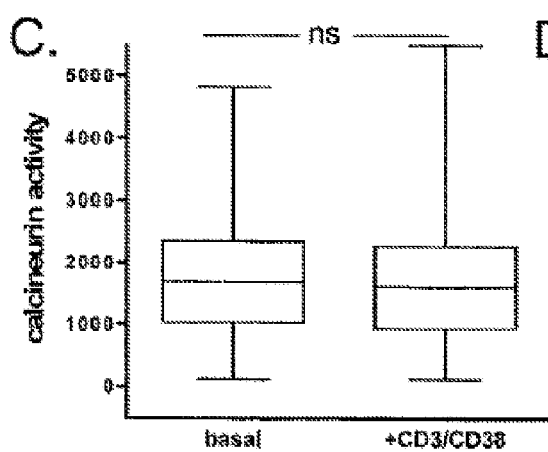
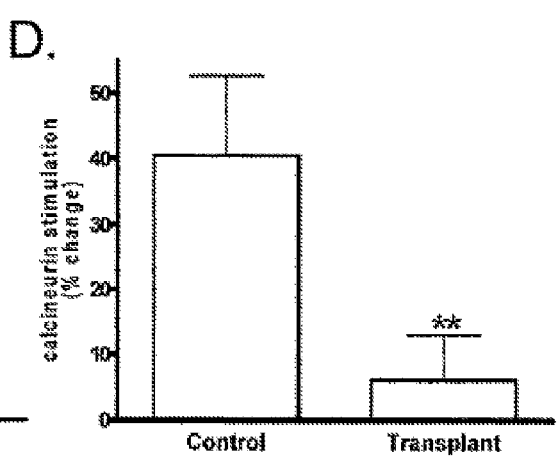
FIG. 5C            FIG. 5D

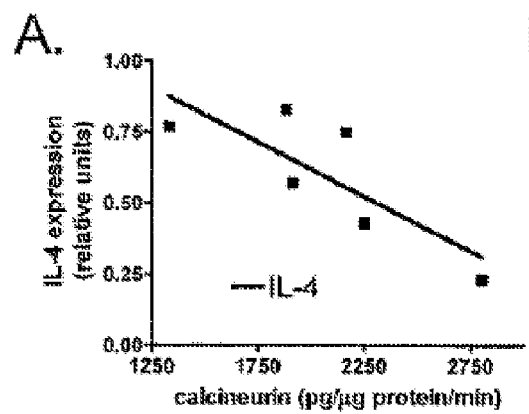
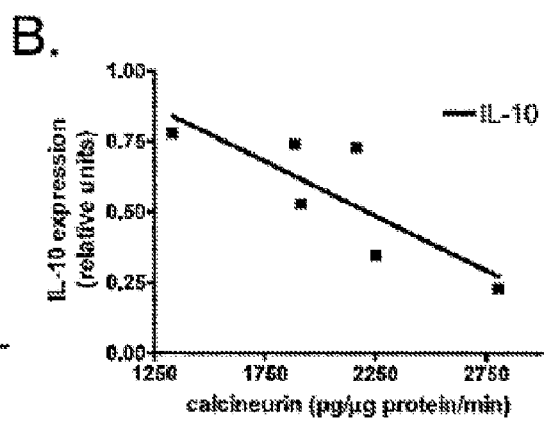
FIG. 7A  FIG. 7B
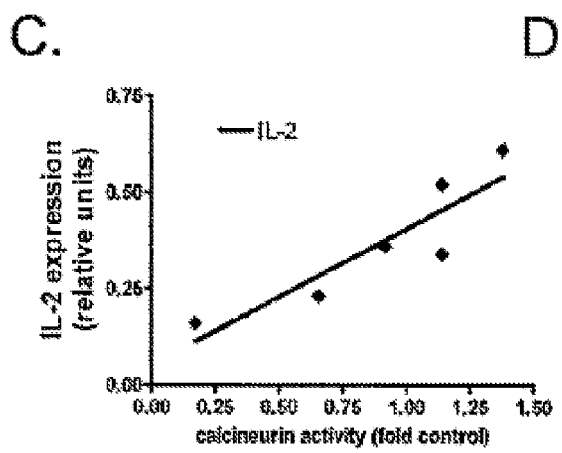
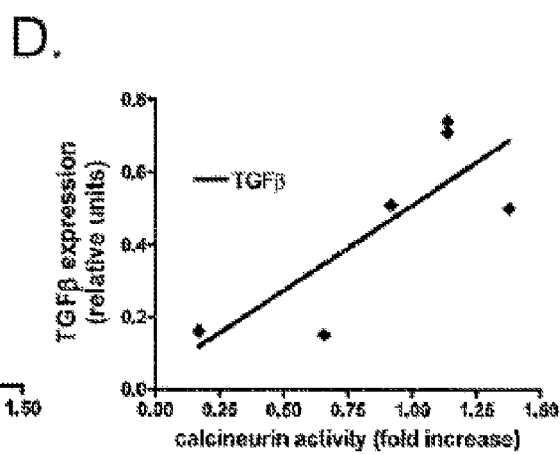
FIG. 7C  FIG. 7D

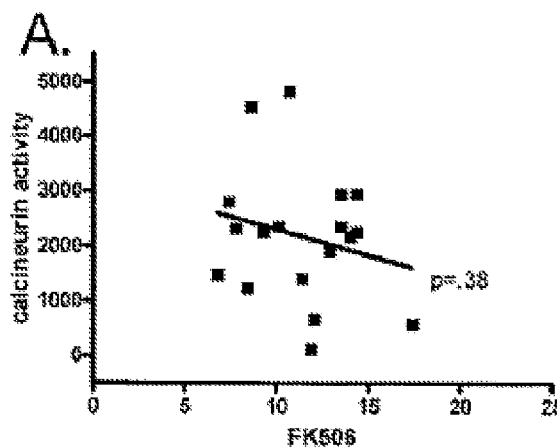
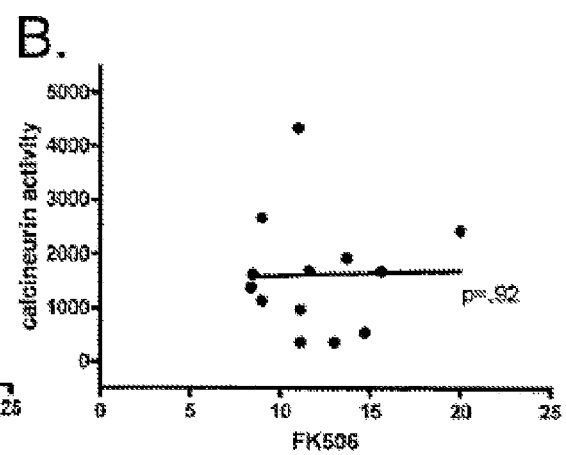
FIG. 9A
FIG. 9B
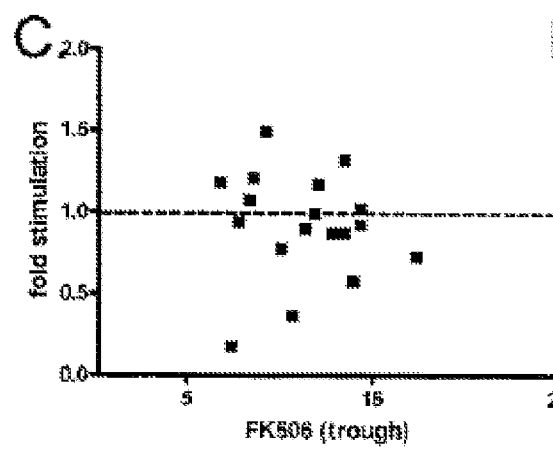
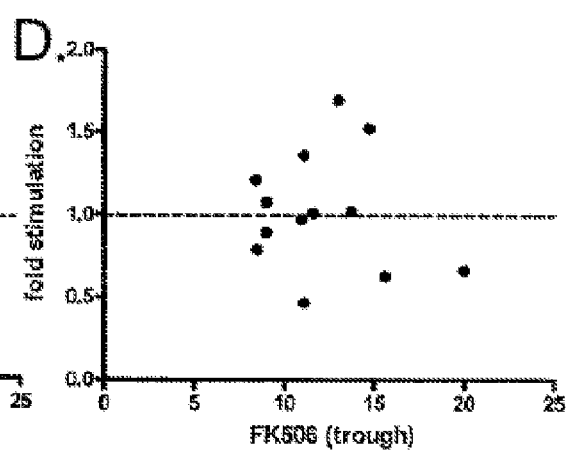
FIG. 9C
FIG. 9D

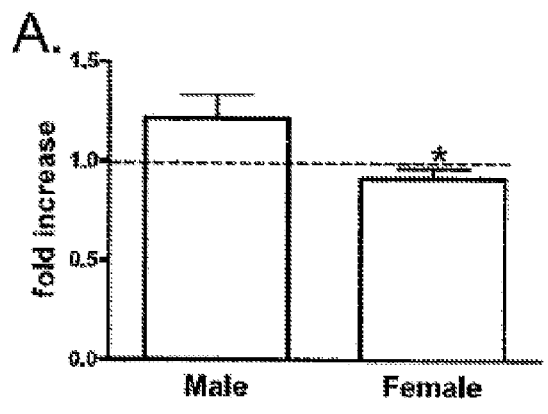
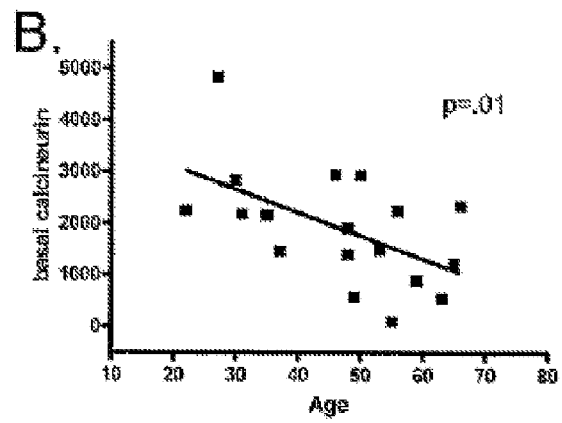
FIG. 10A                FIG. 10B
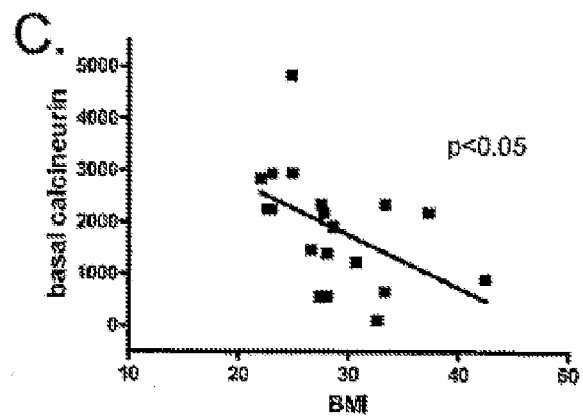
FIG. 10C

SEQUENCE LISTING

<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: synthesized peptide

<400> SEQUENCE: 1

Asp Leu Asp Val Pro Ile Pro Gly Arg Phe Asp Arg Arg Val Ser Val
1               5                   10                  15

Ala Ala Glu

<210> SEQ ID NO 2
<211> LENGTH: 16
<212> TYPE: PRT
<213> ORGANISM: Artificial Sequence
<220> FEATURE:
<223> OTHER INFORMATION: synthesized peptide

<400> SEQUENCE: 2

Ala Ser Pro Gln Thr Ser Pro Trp Gln Ser Pro Ala Val Ser Pro Lys
1               5                   10                  15

METHODS FOR DETERMINING CALCINEURIN ACTIVITY, AND USES IN PREDICTING THERAPEUTIC OUTCOMES

CROSS-REFERENCE TO RELATED APPLICATIONS

This application is a continuation application and claims priority to U.S. patent application Ser. No. 12/669,665 filed May 24, 2010, now abandoned which is a 371 U.S.C. filing of PCT/US2008/071726 filed on Jul. 31, 2008, which claims priority to U.S. Provisional Patent Application Ser. No. 60/962,884, filed Aug. 1, 2007, which are hereby incorporated by reference in their entireties.

STATEMENT ON FUNDING PROVIDED BY THE U.S. GOVERNMENT

This invention was made with government support under NIH Grant No. R01 DK066422 awarded by the U.S. National Institutes of Health of the United States government. The government has certain rights in the invention

FIELD OF THE DISCLOSURE

This disclosure relates to methods of determining activities of protein phosphatases and kinases. The disclosure further relates to methods of clinical monitoring of calcineurin activity and immunosuppression in patients, and which may be used to predict transplant acceptance in patients.

BACKGROUND

Calcineurin is a calcium-dependent, serine/threonine phosphatase that is a signal transduction mediator involved in a variety of pathways including T cells. There are 3 isoforms of the catalytic subunit of calcineurin—$\alpha$, $\beta$, and $\gamma$—and our work and that from other laboratories have identified unique and distinct roles for the $\alpha$ and $\beta$ isoforms. Importantly, the $\beta$ isoform appears to be the primary isoform required for normal activity of T cells.

The addition of calcineurin inhibitors (cyclosporin A and FK506) (calcineurin inhibitors) to immunosuppressive regiments reduces the incidence of acute allograft rejection and effectively doubles one-year survival of kidney transplant patients. However, long-term graft survival has improved far less significantly, with only 66% and 78% of deceased donor and living donor recipients, respectively, surviving 5 years. This statistic is even more striking when considered for different racial groups. 80% of Caucasians who receive living donor organs survive for 5 years while only 64% of African Americans live that long. Similar trends are observed for recipients of deceased donor organs; there is a 70% survival rate for Caucasians and only 55% for African Americans. Understanding mechanisms that contribute to disparate outcomes for transplant patients is an area of tremendous importance. Despite considerable effort, no consensus on the underlying causes has been reached that adequately explains racial disparities in long-term outcomes.

Cyclosporin A (CsA) and FK506 exert their immunosuppressive action by inhibition of the calcium-dependent phosphatase calcineurin. Calcineurin is known to be activated downstream of the T cell receptor and regulates transcription factors including the Nuclear Factor of Activated T cells (NFATs). NFATc proteins, in turn, control expression of cytokines including IL-2 and IL-4. Blockade of calcineurin/NFAT activity inhibits T cell activity and results in immune suppression. Although CsA has been clinically used for more than 20 years and FK506 over a decade, target blood levels for maintenance immunosuppression have yet to be properly defined. Therapeutic monitoring of trough CI concentration has proven to be a poor clinical indicator as some patients experience rejection in the presence of adequate or even high blood CI concentrations, whereas others develop toxicity even when blood trough concentrations are low. Discrepancies between CI dose and clinical immune suppression suggest that calcineurin activity itself may be a source of variability. However, there have been only limited studies that directly measure calcineurin activity, and there is no data regarding factors which may affect the calcineurin sensitivity to inhibition by cyclosporin and FK506.

SUMMARY

One aspect of the present disclosure encompasses methods for determining a protein kinase or phosphatase activity in a biological sample. The methods of the disclosure may be adapted for determining the calcineurin activity in a biological sample. The methods of the disclosure may further allow monitoring of the effects of immunosuppressants, and in particular calcineurin inhibitors, on calcineurin activity. This data may then be used as a predictor of the efficacy of immunosuppressants in a patient, or the likely outcome of a transplant in a patient. The methods of this aspect of the disclosure, therefore, comprise: contacting in a reaction mix a first test sample and a fluorescently-labeled peptide substrate capable of being modified by a protein phosphatase or a protein kinase, under conditions allowing the kinase or phosphatase to modify the phosphorus status of the peptide; contacting the reaction mix with a $TiO_2$ matrix, thereby partitioning fluorescently-labeled phosphorylated peptide from fluorescently-labeled non-phosphorylated peptide; and determining the fluorescence of the fluorescently-labeled non-phosphorylated peptide, thereby determining a protein kinase or phosphatase activity.

The embodiments of this aspect of the disclosure may further comprise: providing a first test sample; admixing a fluorescently-labeled phosphorylated peptide substrate, a reaction buffer, and a first test sample to form a first reaction mix; incubating the first reaction mix under conditions allowing a phosphatase to dephosphorylate the fluorescently-labeled phosphorylated peptide; providing a reaction vessel, wherein the reaction vessel is coated with a $TiO_2$ matrix, and wherein the $TiO_2$ matrix is contacted with a binding buffer; delivering the first reaction mix to the coated vessel, and incubating under conditions allowing binding of fluorescently-labeled phosphorylated peptide to the $TiO_2$ matrix; transferring the first reaction mix from the coated well, and determining the amount of fluorescence emitted by the fluorescently-labeled dephosphorylated peptide of the first reaction mix.

In embodiments of the disclosure, the assay methods may further comprise comparing the fluorescence emitted by the first reaction mix with the fluorescence emitted by at least one second test sample comprising a known amount of active calcineurin, thereby determining the amount of calcineurin in the first test sample.

In other embodiments of the disclosure, the assay methods may further comprise comparing the fluorescence emitted by the first reaction mix with the fluorescence emitted by at least one second test sample, wherein the second test sample includes a calcineurin inhibitor.

In another embodiment, the assay method may be configured for high-throughput screening of a plurality of test samples by providing a plurality of test samples, thereby forming a plurality of reaction mixes.

In yet another embodiment of the assay method of this aspect of the disclosure, the fluorescently labeled phosphorylated peptide can be capable of distinguishing a first isoform of calcineurin from a second isoform. The methods of the disclosure may further be configured for predicting the outcome of a transplant in a patient in need thereof Another aspect of the disclosure encompasses methods of determining the response of calcineurin of a human or animal patient to a calcineurin inhibitor, comprising: obtaining from a patient a first cell or tissue test sample and a second cell or tissue sample; determining the level of activity of calcineurin in the first test sample; determining the level of activity of calcineurin in the second test sample in the presence of a calcineurin inhibitor; and comparing the levels of calcineurin activity in the first and second samples, thereby predicting a response of the patient to a calcineurin inhibitor administered thereto.

In one embodiment of this aspect of the disclosure, the prediction of the response of a patient to an administered calcineurin inhibitor further predicts the likely outcome of a transplantation in the patient.

Another aspect of the present disclosure are kits for determining the level of a phosphatase or a kinase activity in a test sample, comprising a container enclosing a fluorescently labeled peptide substrate; and instructions for the use of the peptide in determining the phosphatase or a kinase activity of a test sample, and optionally for predictively determining the outcome of a transplant on a patient.

In one embodiment of the disclosure, the kit may further comprise a reaction vessel coated with a titanium dioxide matrix.

In one embodiment of the disclosure, the peptide substrate is phosphorylated, and the instructions direct the use of the kit to determine a phosphatase activity.

In one embodiment of the disclosure, the peptide substrate is non-phosphorylated, and the instructions direct the use of the kit to determine a kinase activity.

BRIEF DESCRIPTION OF THE FIGURES

Many aspects of the disclosure can be better understood with reference to the following figures.

See the text and examples for a more detailed description of the figures.

FIG. 2A: Reactions were carried out with 0, 0.2, or 0.3 ng of recombinant calcineurin per reaction and then the relative amount of dephosphorylated to phosphorylated peptide was determined by mass spectrometry. Data shown is the ratio of the area under the curve for dephosphorylated RII and phosphorylated RII with each condition. FIG. 2B: Reactions were carried identically as in FIG. 2A, and then incubated with $TiO_2$ matrix in a 96-well plate. After binding, the samples were removed and the relative amount of dephosphorylated to phosphorylated peptide was determined by mass spectrometry. Data shown is the ratio of the area under the curve for dephosphorylated RII and phosphorylated RII with each condition.

FIG. 3A: Calcineurin assays were performs with increasing amounts of recombinant calcineurin in the presence or absence of calcium. Recombinant calcineurin resulted in increased amounts of dephosphorylated peptide in a dose-dependent manner This activity was dependent upon calcium. Data shown are the mean+/−SEM of triplicate reactions. FIG. 3B: Reactions containing 0.2 ng of recombinant calcineurin were carried out along with standard controls to verify calcineurin activity. Heat inactivation of the enzyme, addition of an auto inhibitory peptide, or absence of calcium all significantly reduced activity (ANOVA). Data shown are the mean+/−SEM of triplicate samples compared to a standard curve.

FIG. 4 illustrates the detection of calcineurin-mediated dephosphorylation.

FIGS. 5A-5D illustrate the stimulation and inhibition of calcineurin activity in healthy control subjects.

FIG. 5A shows T cells were isolated from healthy control subjects (n=30), divided into equal aliquots, and then treated with DMSO as a control or anti-CD3/CD28 antibody (1 ng/ml) for 15 minutes to produce maximal calcineurin activation. Samples were then lysed and calcineurin activity determined. Data shown in each column is a box and whisker plot of control and stimulated groups. Anti-CD3/CD28 treatment resulted in a significant increase in T cell calcineurin activity (paired T-test, $p<0.001$).

FIG. 5B shows T cell isolates from a group of control subjects (n=30) were isolated and separated into 4 equal aliquots. Divided samples were treated with DMSO as a control, anti-CD3/CD28, or pre-treated with calcineurin inhibitors cyclosporin A (CsA, 5∥g/ml) or FK506 (5 ng/ml) prior to stimulation with anti-CD3/CD28 antibodies. Lysates were obtained and calcineurin activity was determined. Data shown are box and whisker plots for each treatment group. ANOVA with Tukey's post-test indicated that anti-CD3/CD28 again produced a significant increase in calcineurin activity **$p<0.001$. Both CsA and FK506 pre-treatments blocked stimulation are were not different from control.

FIG. 5C shows T cells were isolated from post-transplant patients who were currently taking calcineurin inhibitors (n-39), divided into equal samples and then treated with DMSO as a control or anti-CD3/CD28 antibodies for 15 minutes. Samples were lysed and calcineurin activity was determined Data are shown in a box and whisker plot for each treatment group. There was no difference in calcineurin activity with anti-CD3/CD28 stimulation (paired T-test).

FIG. 5D shows the percent increase in calcineurin activity was determined for control subjects and transplant patients.

Data shown are the mean±SEM of % change in stimulated calcineurin activity for each study participant (controls n=82, transplant patients n=39). Stimulated calcineurin activity was significantly less in transplant subjects compared to controls (T-test, **p<0.01).

FIGS. 6A-6D illustrate that race is associated with differences in inhibition of anti-CD3/CD28-stimulated calcineurin activity.

Figure 6A:
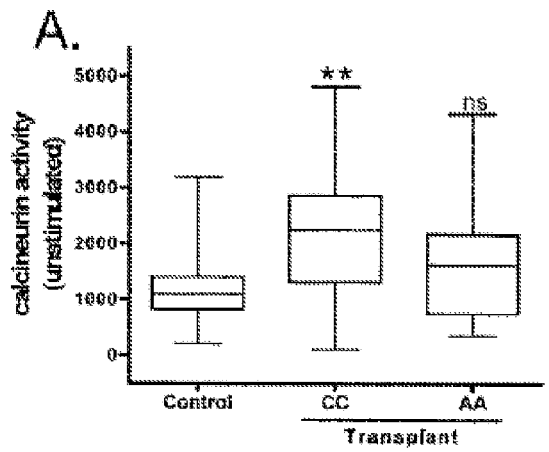

FIG. 6A shows basal calcineurin activity compared in control subjects and transplant patients who self-identified as either Caucasian (CC) (n=18) or African American (AA) (n=19). Data are plotted in the box and whisker format. There was a significant increase in unstimulated calcineurin activity in the CC transplant group compared to the AA group (*p<0.05 ANOVA, Tukey's post-test). Basal levels of calcineurin activity in AA patients were not different from controls.

Figure 6B:
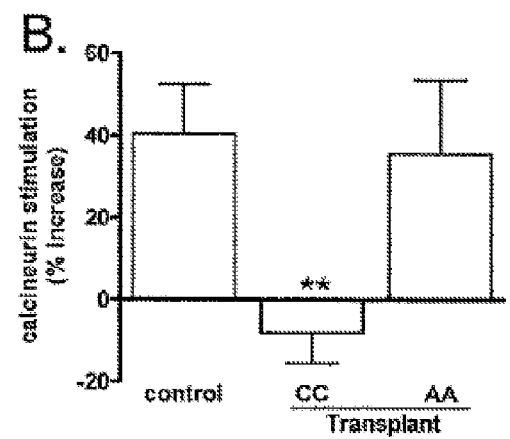

FIG. 6B shows the percent increase in stimulated calcineurin activity was compared for control participants, and CC and AA transplant patients. There was a trend for calcineurin stimulation in the CC transplant group to be lower than both control subjects and AA transplant groups, but the result did not reach significance. Stimulated calcineurin activity in AA patients was not, however, different from that of controls (p<0.01 ANOVA, Tukey's post-test).

Figure 6C:
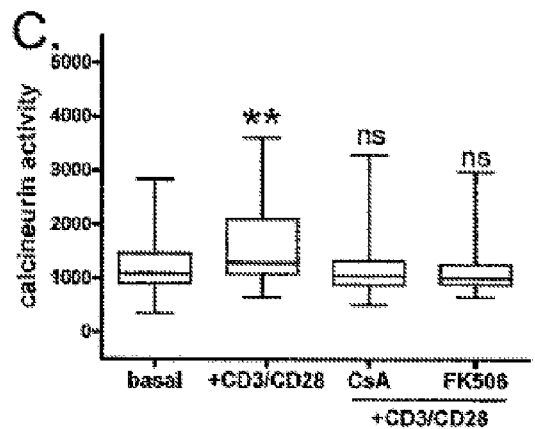

FIG. 6C shows data shown are plotted in box and whisker format for 32 control subjects who self-identify as CC. Anti-CD3/CD28 treatment resulted in a significant increase in calcineurin activity, which was inhibited by both CsA and FK506 (repeated measures ANOVA, Tukey's post-test **p<0.001).

Figure 6D:
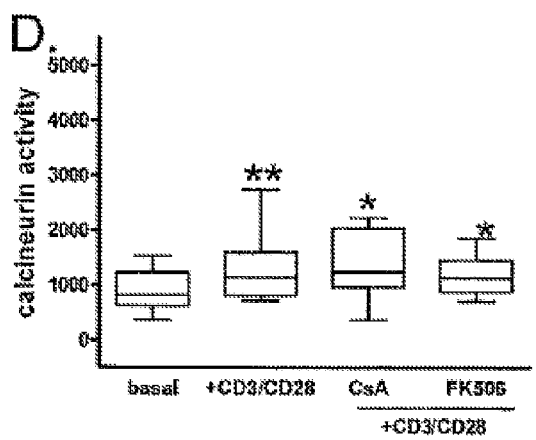

FIG. 6D shows data shown are the results of 44 control subjects who self-identify as AA plotted in box and whisker format. Anti-CD3/CD28 treatment resulted in a significant increase in calcineurin activity, but neither CsA nor FK506 pre-treatment inhibited calcineurin activity; both groups remain significantly higher than basal and not different from CD3/CD28 stimulated samples (repeated measures ANOVA, Tukey's post-test **p<0.001, * p<0.05).

FIGS. 7A-7D illustrate T cell cytokine expression correlation with basal and stimulated calcineurin activity. Isolated T cells from a subset of transplant patients (N=6, 3CC and 3AA) were obtained and conditioned media were collected. Production of a panel of cytokines by T cells were measured using Panomics cytokine array (Fremont, Calif.). Luminescence results were quantified by densitometry and normalized to internal controls. Results for individual cytokines were then compared to basal and fold stimulated calcineurin activities for each patient by linear regression. FIGS. 7A and 7B show IL-4 and IL-10 were significantly correlated with basal calcineurin activity (p=0.056 and p<0.05, respectively). FIGS. 7C and 7D show IL-2 and TGFβ were significantly correlated with fold anti-CD3/CD28 stimulation of calcineurin activity (p<0.05, and p=057, respectively).

FIGS. 8A-8D illustrate racial differences in TGFβ and IFNγ expression. Plasma TGFβ (FIG. 8A) and IFNγ (FIG. 8B) levels were determined for a subset of control subjects (n=40) and transplant patients (n=34) by ELISA. Data shown are the mean±SEM of duplicate assays. *p<0.05, T-test. Next, plasma TGFβ (FIG. 8C) and IFNγ (FIG. 8D) levels were determined for CC and AA transplant patients (n=16 and 16, respectively). Data shown are the mean±SEM of duplicate assays. *p<0.05, T-test.

FIGS. 9A-D illustrate that BP2 peptide enables selective measurement of β activity and not α. Addition of increasing amounts of protein samples into the reaction that contain both alpha and beta (wild type) results in a dose-responsive increase in activity. Addition of protein sample that contains only beta but not alpha also results in a dose-dependent increase.

FIGS. 10A-C illustrate that BP2 peptide detects β-specific activity. We have found that calcineurin can be activated by hyperosmolality and that this activity is lost in cells that lack the beta isoform indicating that activity in response to osmolar stimuli is β-specific. The BP2 peptide also detects changes in calcineurin activity that is consistent with β-specific activity.

DESCRIPTION OF THE DISCLOSURE

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those skilled in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the"

include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Optional" or "optionally" means that the subsequently described circumstance may or may not occur, so that the description includes instances where the circumstance occurs and instances where it does not.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

By "detectably labeled" is meant that a fragment or an oligonucleotide contains a nucleotide that is radioactive, or that is substituted with a fluorophore, or that is substituted with some other molecular species that elicits a physical or chemical response that can be observed or detected by the naked eye or by means of instrumentation such as, without limitation, scintillation counters, colorimeters, UV spectrophotometers and the like. As used herein, a "label" or "tag" refers to a molecule that, when appended by, for example, without limitation, covalent bonding or hybridization, to another molecule, for example, also without limitation, a polynucleotide or polynucleotide fragment provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence, electrochemiluminescence, raman, colorimetric, hybridization protection assay, and mass spectrometry "Peptide" refers to a polymer in which the monomers are amino acid residues which are joined together through amide bonds, alternatively referred to as a polypeptide. A "single polypeptide" is a continuous peptide that constitutes the protein. When the amino acids are alpha-amino acids, either the L-optical isomer or the D-optical isomer can be used, the L-isomers being preferred. Additionally, unnatural amino acids such as beta-alanine, phenylglycine, and homo-arginine are meant to be included. Commonly encountered amino acids which are not gene-encoded can also be used in the present disclosure, although preferred amino acids are those that are encodable. For a general review, see, for example, Spatola, A. F., in Chemistry and Biochemistry of Amino Acids, Peptides and Proteins, B. Weinstein, ed., Marcel Dekker, N.Y., p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Amino acids" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Calcineurin" is known as a calcium ion- and calmodulin-dependent serine-threonine phosphatase. Calcineurin is a $Ca^{2+}$/calmodulin-dependent protein phosphatase and is an element of many intracellular signaling pathways. (Guerini & Klee, Proc. Natl. Acad. Sci. USA 86:9183-9187 (1989)). The protein has been identified in eukaryotic cells ranging from yeast to mammals.

The term "fluorescently labeled" as used herein refers to conjugating to a peptide substrate a fluorescent moiety. A variety of different label moieties are available for use in the substrates of the present disclosure. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes.

The term "kinase" as used herein refers to any enzyme capable of adding a phosphate group to an amino acid side-chain of a protein, polypeptide or a peptide.

The term "phosphatase" as used herein refers to an enzyme caable of removing a phosphate group from a protein, polypeptide or a peptide by a hydrolytic reaction.

Discussion

The present disclosure encompasses methods for the determination of enzyme activity that modifies the phosphorylation status of a peptide or protein, either by removal of a phosphor-group by a phosphatase, or by the addition of a phospho-group by a kinase. The assays of the disclosure may be configured to provide data as to the effect on the modifying enzyme activity of an effector such as, but not limited to, an inhibitor. The assay methods of the disclosure provide a fluorophore-labeled peptide that may act as a substrate for the phosphatase or the kinase.

In the case of the phosphatases, the peptide is further phosphorylated on at least one of the amino acids of the peptide sequence. After allowing the peptide substrate to react with a test sample having a phosphatase activity, the dephosphorylated peptide and the phosphorylated peptide substrate are partitioned by contacting with a $TiO_2$ matrix that specifically binds the phosphorylated peptide. The supernatant above the matrix comprises the dephosphorylated peptide, which may be detected by fluorescence after removal from the matrix/substrate layer. It is contemplated that the amino acid sequence of the peptide substrate may be any sequence that is specific for the phosphatase, the activity of which is to be detected. It is further contemplated that the sequence may be such as to be capable of distinguishing isoforms of a phosphatase. For example, the substrate peptide may have, but is not limited to, the amino acid sequence according to SEQ ID NO.: 1 or 2, wherein the peptides can serve as specific substrates for the phosphatase calcineurin, and wherein SEQ ID NO.: 2 is specific for one isoform of calcineurin, and not others.

In the case of kinases, the substrate peptide having a label attached thereto, but unphosphorylated, will be combined with a phosphate source such as ATP, and a test sample having the kinase activity. After a suitable reaction time, the products of the reaction are again contacted with a TiO$_2$ matrix, to which the newly phosphorylated peptide substrate specifically binds. After washing away of the unbound non-phosphorylated peptide, the bound peptide may be eluted for fluorescence determination, or the fluorescence determined in situ in the matrix.

The present disclosure, therefore, in particular provides methods for determining the level of activity of the phosphatase calcineurin in a biological sample derived from a human or animal patient. Embodiments of the assays may be used to determine the response of the calcineurin activity of a patient to a calcineurin inhibitor, which provides predictors for the outcome of transplantation and/or immunosuppression efficacy. Information from the response of the enzyme to a potential inhibitor may further direct the physician to adjust a regimen of therapeutic agents that may increase the acceptance of the patient towards a transplanted organ, and reduce rejection thereof.

The methods of the present disclosure allow for the assaying of the calcineurin activity by a conventional assay based on measuring the release of a radioactive phosphorus label from a peptide substrate, or by using a fluorescence-based assay that provides several advantages compared to the more traditional assay.

Fluorescence-Based Calcineurin Assay

Calcineurin is a calcium-dependent, serine/threonine phosphatase that is involved in a variety of signaling pathways. Calcineurin is distinct among phosphatases because its activity requires calcium and is not sensitive to inhibition by compounds that block the related phosphatases PP1A and PP2A. Therefore, the most common methods to measure calcineurin activity rely on calcium-dependent dephosphorylation of a substrate derived from the RII subunit of protein kinase A in the presence of PP1A/PP2A inhibitors.

In an established assay method for calcineurin activity, a peptide substrate is incubated with protein kinase A and $^{32}$P$\gamma$[ATP] under appropriate conditions to phosphorylate the peptide with a radioactive residue. The labeled substrate is then purified and used within a short period of time as a substrate for calcineurin. To measure calcineurin activity, equal parts of cell lysate, reaction mixture, and labeled substrate are incubated at 30° C. for 10 minutes before the reaction is terminated. To determine how much of the phosphorylated peptide has been dephosphorylated, individual columns are prepared for each reaction containing pre-charged ion-exchange resin. Reactions are loaded on the column and unincorporated phosphate, which does not bind the resin, is eluted. The amount of radioactivity in the eluted fractions is then measured in a scintillation counter and used to quantify calcineurin activity. In general, the method has several drawbacks including the use of radioactive phosphate for labeling of the peptide substrate, background due to unincorporated phosphate, reliance upon ion exchange to separate phosphorylated from non-phosphorylated peptide, and the final measurement of free phosphate to represent calcineurin activity. These factors increase variability of the data and reduce reproducibility of the assay.

Embodiments of the disclosure provides an assay to determine calcineurin activity using well-characterized reaction conditions, a fluorescently labeled phosphopeptide substrate, and separation of dephosphorylated substrate by titanium-oxide. The methods according to the present disclosure are rapid, involve no radioactivity, and are suitable for high throughput assays. Furthermore, with the use of a standard curve, precise measurements of calcineurin activity are attainable.

Figure 1:
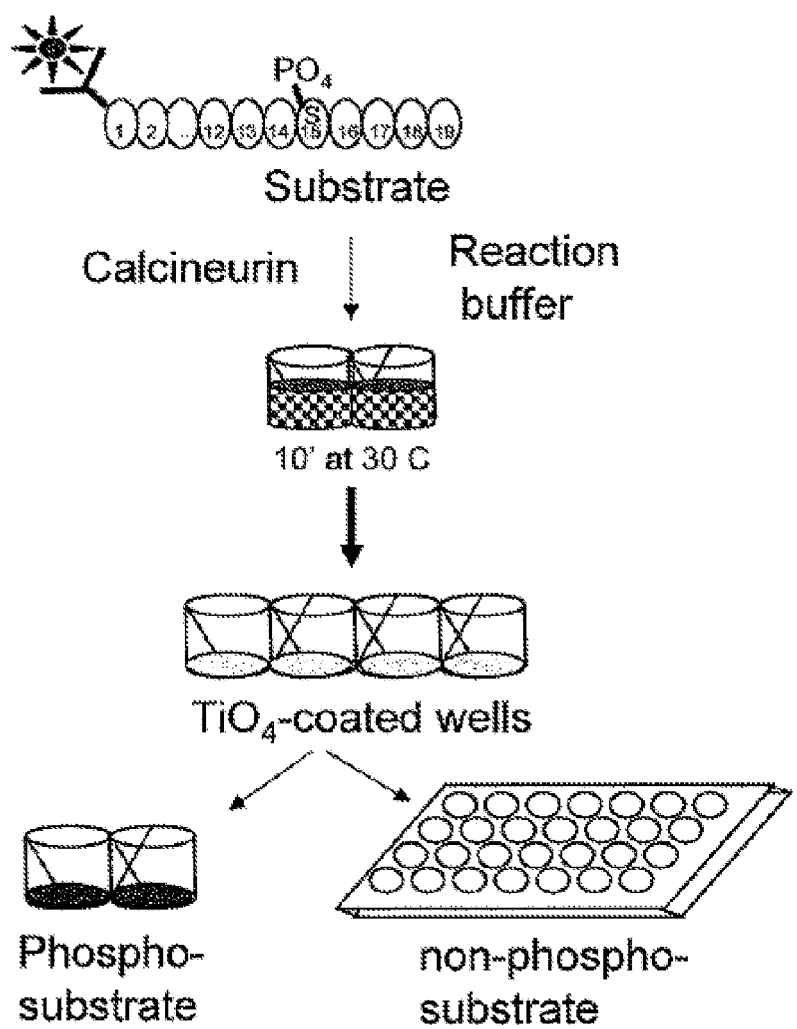
FIG. 1 illustrates a schematic of a fluorimetric calcineurin assay. The RII peptide substrate is synthesized with a phospho-Serine 15 residue and an amino-terminus fluorescent tag. In a 96-well plate, the labeled substrate is mixed in equal parts with reaction buffer and sample and allowed to incubate at 30° C. for 10 minutes. Each well is then transferred to a 96-well plate coated with titanium-oxide ($TiO_2$) followed by gentle shaking to allow binding of phosphorylated substrate. Finally, the total contents of each well is then moved to a new 96-well plate and the amount of dephosphorylated peptide determined by fluorimetry at 485 nm excitation and 528 nm emission.

The steps of the methods of the present disclosure are illustrated in FIG. 1. In brief, a peptide is synthesized that can be phosphorylated at the Ser-15 position during peptide synthesis itself, thereby eliminating the need for enzymatic labeling. In embodiments of the methods according to the present disclosure, the peptide may have, but is not limited to, the amino acid sequence NH2-DLDVPIPGRFDRRVSVAAE-COOH (SEQ ID NO.: 1) The RII peptide, Fluoresceinyl-DLDVPIPGRFDRRVSVAAE, and its phosphorylated analog (Fluoresceinyl-DLDVPIPGRFDRRVpSVAAE where pS=L-phosphoserine) are variants of the peptide SEQ ID NO.: 1 for use in the methods of the disclosure, and in particular for the detection of calcineurin activity. The peptide was also generated with a fluorescent moiety at its amino-terminus, the fluorescent label being, but not limited to, fluorescein or TAMRA. Next, the tagged, labeled peptide can be incubated with the desired lysate for 10 minutes at 30° C.

The methods of the present disclosure make use of the property that TiO$_2$ is highly specific for binding of phosphorylated peptides to separate phosphorylated from non-phosphorylated peptide. To this end, plates coated with titanium oxide are utilized. Reaction mixes are transferred to the TiO$_2$ plate, followed by gentle shaking at room temperature for 5 minutes to allow binding of the phosphorylated peptide. Dephosphorylated peptide, which does not bind to the TiO$_2$ matrix, can then be transferred to a new plate and quantified by fluorimetry of the fluorescein tag.

To validate this new method, mass spectrometry was used to verify that the labeled, tagged peptide can be dephosphorylated by calcineurin. Phosphorylated, fluorescein-tagged peptide was used as a substrate for calcineurin under established reaction conditions. After stopping the reaction with 0.1% acetic acid in 10% acetonitrile, the samples were analyzed by mass spectrometry.

Figure 2A:
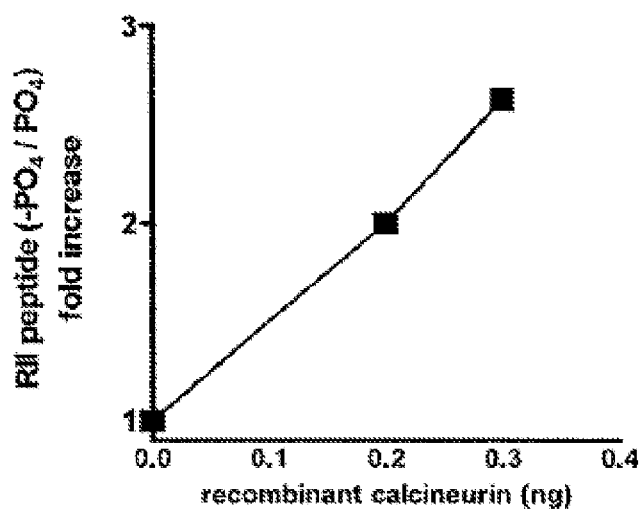
FIGS. 2A and 2B show the validation of fluorescein-labeled RII peptide by mass spectrometry.
Figure 2B:
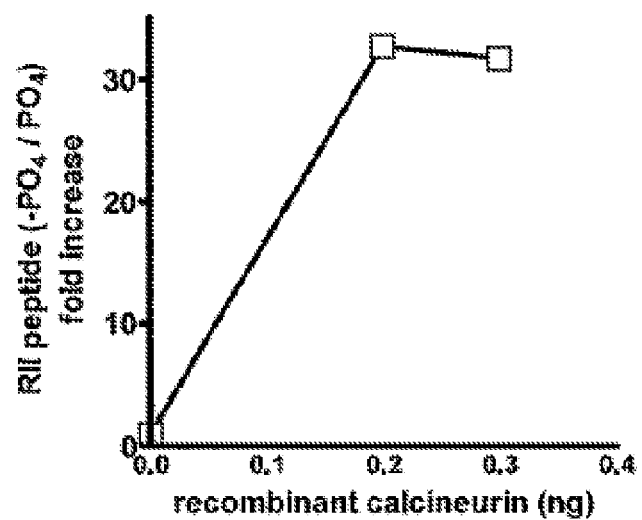

FIG. 2A shows that recombinant calcineurin stimulated a dose-responsive increase in the relative amount of dephosphorylated to phosphorylated peptide. TiO$_2$ matrix effectively separates dephosphorylated from phosphorylated peptide. Reactions were performed identically as in FIG. 2A, but with the additional step of incubating the reactions in TiO$_2$ coated wells for 5 minutes. The amount of dephosphorylated peptide in the unbound fraction was analyzed by mass spectrometry. FIG. 2B shows that there was a 30-fold increase in the amount of dephosphorylated peptide in the unbound fraction with the addition of recombinant calcineurin.

Figure 3A:
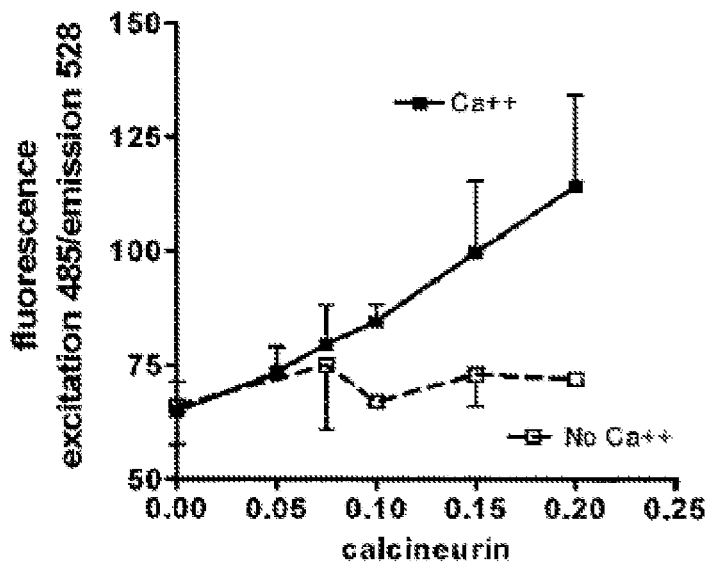
FIGS. 3A and 3B illustrate dose-responses with recombinant calcineurin.

After confirming that the labeled peptide could be dephosphorylated, and the TiO$_2$ effectively separated phosphorylated from non-phosphorylated peptide, the assay was characterized. Reactions containing increasing amounts of recombinant calcineurin in either normal reaction buffer or calcium-free reaction buffer were analyzed. Calcineurin in normal buffer resulted in dephosphorylation of the peptide in a dose-dependent manner In the absence of calcium, however, there was no increase in dephosphorylation, as shown in FIG. 3A.

Figure 3B:
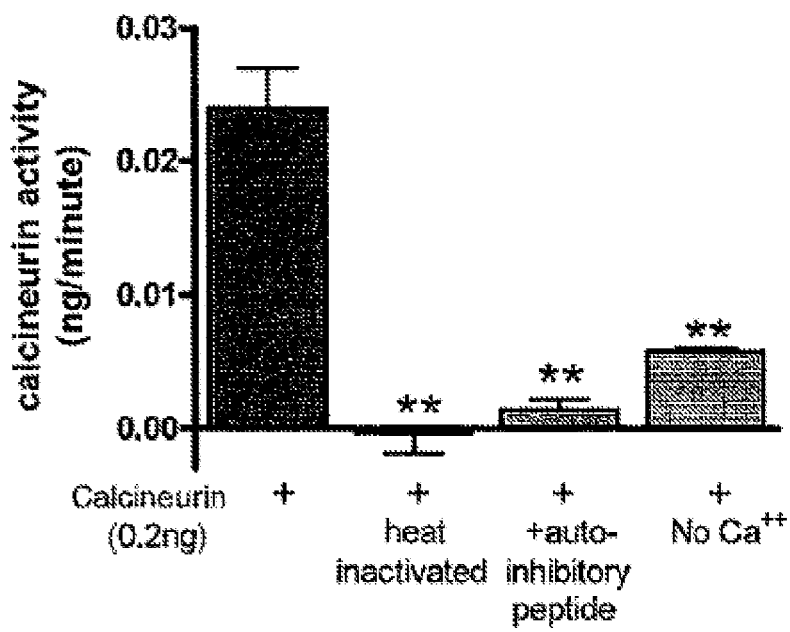

Reactions using 0.2 ng of recombinant calcineurin along with standard controls for calcineurin activity, including heat inactivation of the recombinant enzyme, addition of an auto-inhibitory peptide, absence of calcium, and chelation of calcium with EGTA were investigated. Dephosphorylation by 0.2 ng calcineurin was significantly reduced (ANOVA) by each of these conditions, as shown in FIG. 3B.

Figure 4A:
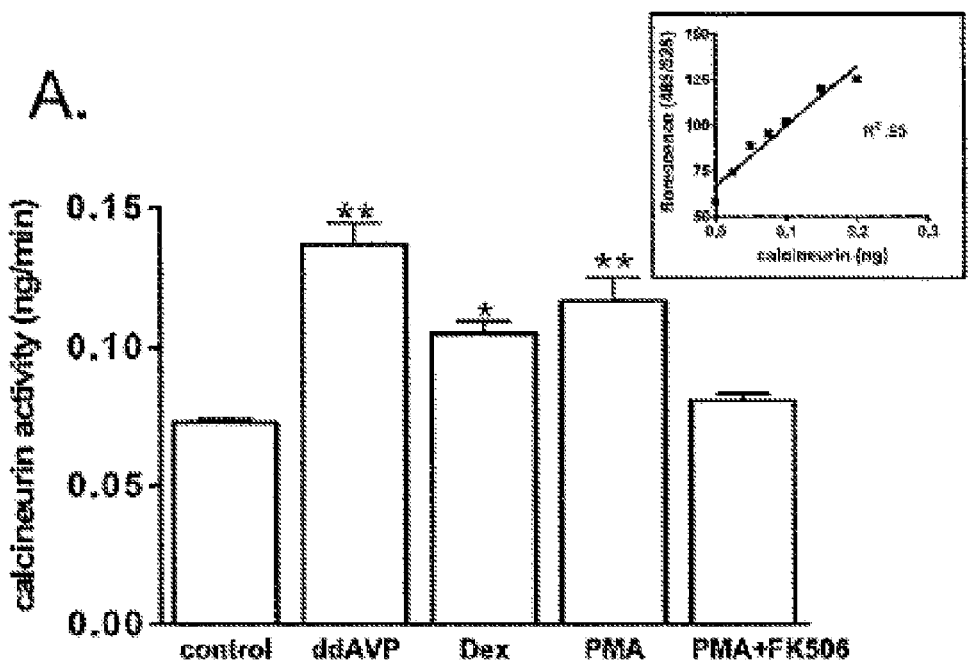
FIG. 4A: Cultured renal fibroblasts were treated with a variety of stimuli including arginine vasopressin (AVP), dexamethasone, and phorbol myristate acetate (PMA) to induce calcineurin activity. In addition, some cells were pre-treated with calcineurin inhibitors prior to addition of PMA. Cells were lysed according to previously established methods and then calcineurin activity was determined. Data shown is the mean+/−SEM of triplicate samples compared to a standard curve.
Figure 4B:
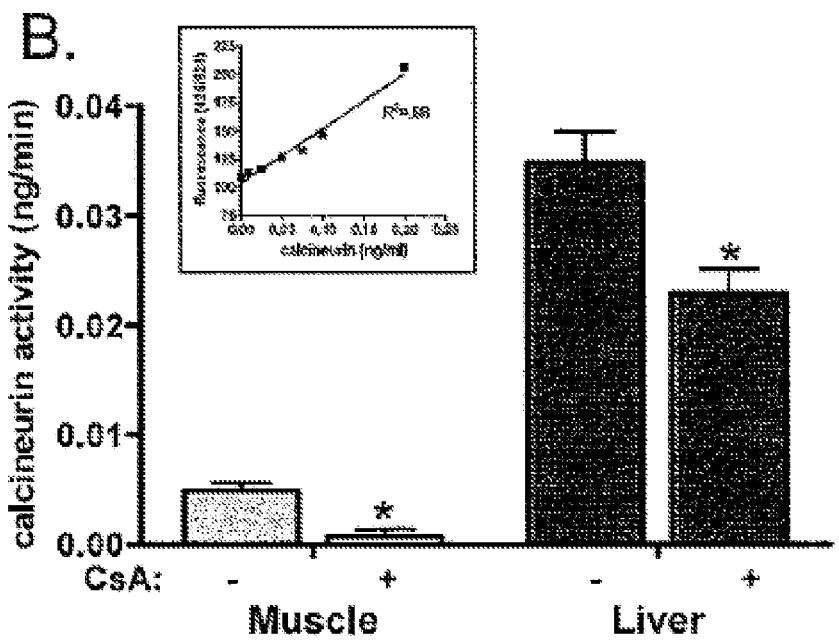
FIG. 4B: Mice were treated with cyclosporin A for three days to inhibit calcineurin activity and then liver and muscle samples were harvested. Tissues were lysed according to previously established methods and calcineurin activity determined Data shown are the mean+/−SEM of triplicate samples compared to a standard curve.

The use of the new calcineurin assay in two systems was explored. FIG. 4A shows the result of calcineurin stimulation by a variety of agents in cultured primary renal fibroblasts. When the absorbance values obtained were compared to a standard curve of recombinant calcineurin run simultaneously, a determination of calcineurin activity in each condition can be made. Arginine vasopressin (AVP), dexamethasone, and phorbol myristate acetate (PMA) each significantly stimulated calcineurin activity. Pre-treatment with the calcineurin inhibitor FK506 blocked stimulation by PMA. Next, protein lysates were collected from liver and muscle samples of mice treated with vehicle alone or treated daily with 20 mg/kg cyclosporin A. Calcineurin assays were performed on 1 µg of total protein. Results indicated that there is significantly more calcineurin activity per µg protein in the liver compared to muscle. Cyclosporin treatment significantly decreased calcineurin activity in both tissues (FIG. 4B).

Acidic peptides (other than phosphopeptides) also show affinity for $TiO_2$. The RII peptide is, in fact, rather acidic even when not including phospho-Ser-15 (5 negative and 3 positive charges); however this does not negatively influence the ruggedness and reproducibility of the assay. $^{32}$P-based assays are very specific as they measure inorganic phosphate released upon the action of the phosphatase. The embodiments of the assay method of the present disclosure, on the other hand, measure fluorescence of the probe attached to unbound peptide released to solution due to the loss of phosphate (which causes loss of binding affinity to $TiO_2$). However, it is possible that the fluorescence probe may also be released in solution by the action of a protease, e.g. a tryptic-like enzyme present in the biological material, cleaving the substrate at the C-terminal side of arginines. In such case, peptide fragments such as Fluoresceinyl-DLDVPIPGR will be released simulating phosphatase activity, and thereby presenting false positive results. Hence, inclusion of protease inhibitors is necessary to minimize such artifacts.

The fluorimetric method of the present disclosure is not limited to the incorporation of a fluorescein tag, and it is contemplated that the peptides of the assay may be modified with other fluorescent moieties. Fluorescein can be quenched by common reagents including dithiothreitol and its excitation can be altered with pH and light exposure. Use of fluoresceine requires the reaction to be protected from light and neutralized prior to fluorimetry. Other tags suitable for incorporation into the peptide substrates for use in the methods of the present disclosure include, but are not limited to such as TAMRA, which may be less pH- and light-sensitive.

To further evaluate the reproducibility of the method, 14 separate samples with 6 replicate reactions were analyzed. The intra-assay variability was 9.35%, a better variability rate than achieved with previous methodologies.

The present disclosure further encompasses assays that comprise the peptide substrate that can be selectively dephosphorylated by the β isoform of calcineurin and not the α isoform. The amino acid sequence of the isoform-specific peptide substrate is based on a portion of the NFATc protein, a known substrate of calcineurin, which has been modified to improve isoform selectivity and ease of synthesis. The amino acid sequence of the peptide is ASPQTSPWQSPAVSPK (SEQ ID NO.: 2) wherein the Ser-6 position may be phosphorylated. A fluorescently labeled version of the peptide is as follows: ASPQT(pS)PWQSPAVSPK with an N-terminal fluorescent TAMRA group and a C-terminal amide group, although it is contemplated that a fluorescent group other than TAMRA may be substituted without affecting the efficacy of the substrate.

As shown in FIGS. 9 and 10, this peptide can be dephosphorylated by β calcineurin but not α (FIG. 9) and that the peptide selectively detects activation of β-specific calcineurin activity (FIG. 10).

Predictive Assay for Assessing Patient's Response to Transplantation and Immunosuppression Therapies Calcineurin inhibitors have been a cornerstone of post-transplant immune suppressing regiments for over 2 decades. During that time, short-term survival rates have improved remarkably. Current treatment strategies, however, are not yet sufficient to improve long-term outcomes to a similar degree. Variability in response to calcineurin inhibitors may be an important part of therapeutic limitations. While dose ranges have been generally established, it has long been known that there is little correlation between blood level of calcineurin inhibitor and rejection, or the development of complications including nephrotoxicity. In addition, it is apparent that even with optimal calcineurin management, some individuals such as African Americans remain at higher risk for rejection. While there has been considerable effort to identify factors that may contribute to differences in racial disparities post-transplantation, no combination of societal or medical factors appears to completely answer the question. One factor that may explain both the lack of correlation between therapeutic levels and outcome, as well as the relatively higher risk of some patient populations, appear to be differences in the enzymatic response of calcineurin to pharmacological inhibitors.

There is a striking difference in calcineurin inhibitor efficacy in Caucasian (CC) and African American (AA) study participants. AA control subjects are resistant to both cyclosporin- and FK506-mediated inhibition of calcineurin activity and AA transplant recipients continued to respond normally to T cell stimuli despite therapeutic levels of FK506 and cyclosporin.

The data point strongly to multiple, distinct actions of the calcineurin enzyme. There were changes in both the basal levels and the degree of calcineurin stimulation and both activities are modulated by transplantation and race. For example, transplant patients as a whole have significantly higher basal levels of calcineurin (1811±174 versus 1133±103 pg/µg protein/min, p<0.05). Considering that all transplant patients were currently receiving standard immunosuppressant regiments including calcineurin inhibitors, this result was surprising.

Likewise, race appears to correlate with calcineurin activity. Caucasian transplant patients had significantly higher basal calcineurin levels and CC control subjects had slightly higher levels than AA control subjects (not statistically significant). There is a stronger effect of calcineurin inhibitors on stimulation of T cell calcineurin. As a group, calcineurin response to anti-CD3/CD28 co-stimulation in transplant patients was significantly less than that of the control subjects (8% versus 41%), indicating that the main effect of immune suppression is the result of blocking stimulation of calcineurin as opposed to calcineurin activity as a whole. It is therefore highly significant that this is the aspect of calcineurin activity that is the most affected by race.

AA control patients are virtually resistant to FK506- and cyclosporin-mediated inhibition of anti-CD3/CD28 co-stimulation. It is also of interest to note that there is a significant correlation between the degree of CsA-mediated inhibition and FK506-mediated inhibition in both CC and AA control subjects, as shown in Table 5, suggesting that lack of calcineurin inhibition is not specific to the mechanism of action of either drug.

TABLE 5

Multi-variate analysis of control participants by race

| | Basal | | FK5/basal | | Fold Stim. | | FK5/CD3 | | CsA/CD3 | |
|---|---|---|---|---|---|---|---|---|---|---|
| Race | CC | AA | CC | AA | CC | AA | CC | AA | CC | AA |
| 1 Age | p = 09 | ns | ns | ns | ns | ns | ns | ns | ns | ns |
| BMI | ns | ns | p = .03 | ns | p < .01 | ns | ns | ns | ns | ns |
| WBC | ns | ns | ns | p = .01 | ns | ns | ns | p ~ 09 | ns | p = 04 |
| Lymphs | ns | ns | ns | p = .01 | ns | ns | ns | p = .01 | ns | ns |
| Gender | ns | ns | ns | ns | ns | ns | ns | ns | ns | ns |
| FK5/basal | ns | ns | | | | | | | | |
| Fold stimulation | ns | p = <.01 | ns | ns | | | | | | |
| FK5/CD3 | ns | p < .01 | ns | ns | ns | ns | | | | |
| CsA/CD3 | ns | p = 06 | ns | p = .12 | ns | ns | p = 08 | p < 01 | | |

In evaluating the data, elevated levels of basal activity in CC transplant patients reflected a maximal activity, thereby providing an explanation for decreased stimulation in this group. However, linear regression analyses indicated no significant correlation between basal and stimulated calcineurin activities for either the transplant group or the control subjects. There was no significant correlation between basal and stimulated calcineurin activity in either CC or AA controls (Table 5).

Additional factors were examined to determine if other differences between CC and AA patients could account for the changes observed. For example, AA patients in our study cohort were more likely to have received a transplanted organ from a deceased donor compared to CC patients. However, when compared, basal and stimulated activities of calcineurin between CCs receiving living donor kidneys and deceased donor kidneys showed no difference, suggesting that donor source does not account for differences in basal and stimulated calcineurin we find. Similarly, while there were some affects of pre-transplant diagnoses (for example, diabetic transplant patients had, in general, lower basal calcineurin activity than patients with other diagnoses) race consistently correlated with lower basal levels and higher stimulated calcineurin activity independent of diagnoses.

Linear regression analyses of T cell cytokine production and basal and stimulated calcineurin activities resulted in a novel finding that different aspects of calcineurin correlate with changes in different cytokines. More specifically, basal calcineurin activity correlated with levels of the Th2 cytokines IL-10 and IL-4 while stimulated calcineurin correlated with TGFβ and IL-2, both Th1 cytokines.

The data show that CC transplant patients have the combined "profile" of high basal calcineurin and low stimulated calcineurin. If those patterns are applied to results of our cytokine study, the outcome would be high levels of anti-inflammatory Th2 cytokines and low levels of pro-fibrotic, Th1 cytokine. In contrast, AA patients continue to have high levels of stimulated calcineurin activity despite therapeutic levels of calcineurin inhibitors and lower basal levels of calcineurin compared to CC patients. This translates to low levels of Th2 cytokines and high levels of Th1. It is likely, therefore, that racial differences in calcineurin enzymatic activity may underlie disparities in clinical outcomes.

It is shown, therefore, that there is a racial distinction in the effectiveness of calcineurin inhibitors to block T cell stimulation of calcineurin activity. Importantly, changes in stimulated calcineurin activity correlate with regulation of pro-fibrotic cytokines. Together, these data provide a new mechanism for racial disparities in long-term survival following organ transplantation.

One aspect of the present disclosure encompasses methods for determining a protein kinase or phosphatase activity in a biological sample, comprising: contacting in a reaction mix a first test sample and a fluorescently-labeled peptide substrate capable of being modified by a protein phosphatase or a protein kinase, under conditions allowing kinase or phosphatase to modify the phosphorus content of the peptide; contacting the reaction mix with a $TiO_2$ matrix, thereby partitioning fluorescently-labeled phosphorylated peptide from fluorescently-labeled dephosphorylated peptide; and determining the fluorescence of the fluorescently-labeled dephosphorylated peptide, thereby determining a protein kinase or phosphatase activity.

The embodiments of this aspect of the disclosure may further comprise: providing a first test sample; admixing a fluorescently-labeled phosphorylated peptide substrate, a reaction buffer, and a first test sample to form a first reaction mix; incubating the first reaction mix under conditions allowing a phosphatase to dephosphorylate the fluorescently-labeled phosphorylated peptide; providing a reaction vessel, wherein the reaction vessel is coated with a $TiO_2$ matrix, and wherein the $TiO_2$ matrix is contacted with a binding buffer; delivering the first reaction mix to the coated vessel, and incubating under conditions allowing binding of fluorescently-labeled phosphorylated peptide to the $TiO_2$ matrix; transferring the first reaction mix from the coated well to a vessel containing ammonium hydroxide; and determining the amount of fluorescence emitted by the fluorescently-labeled dephosphorylated peptide of the first reaction mix.

In embodiments of the methods of this aspect of the disclosure the steps may further comprise: providing a first test sample; admixing a fluorescently-labeled non-phosphorylated peptide substrate, a reaction buffer, and a first test sample to form a first reaction mix; incubating the first reaction mix under conditions allowing a kinase to phosphorylate the fluorescently-labeled phosphorylated peptide; providing a reaction vessel, wherein the reaction vessel is coated with a $TiO_2$ matrix, and wherein the $TiO_2$ matrix is contacted with a binding buffer; delivering the first reaction mix to the coated vessel, and incubating under conditions allowing binding of fluorescently-labeled phosphorylated peptide to the $TiO_2$ matrix; transferring the first reaction mix from the coated well to a vessel containing ammonium hydroxide; and determining the amount of fluorescence emitted by the fluorescently-labeled dephosphorylated peptide of the first reaction mix.

In embodiments of the disclosure, the assay methods may further comprise comparing the fluorescence emitted by the first reaction mix with the fluorescence emitted by at least one second test sample comprising a known amount of active calcineurin, thereby determining the amount of calcineurin in the first test sample.

In other embodiments of the disclosure, the assay methods may further comprise comparing the fluorescence emitted by the first reaction mix with the fluorescence emitted by at least one second test sample, wherein the second test sample includes a calcineurin inhibitor.

In another embodiment, the assay method may be configured for high-throughput screening of a plurality of test samples by providing a plurality of test samples, thereby forming a plurality of reaction mixes.

In the embodiments of this aspect of the invention, the fluorescently labeled phosphorylated peptide can have an amino acid sequence selected from SEQ ID NO.: 1 and SEQ ID NO.: 2.

In another embodiment, the fluorescently labeled phosphorylated peptide is capable of distinguishing a first isoform of calcineurin from a second isoform.

In another embodiment of the disclosure, the fluorescently labeled phosphorylated peptide is capable of being specifically dephosphorylated by the β-isoform of calcineurin and has the amino acid sequence according to SEQ ID NO.: 2.

In one embodiment, the fluorescently labeled phosphorylated peptide is phosphorylated on the Ser-15 position.

In yet another embodiment of the assay method of this aspect of the disclosure, the fluorescently labeled phosphorylated peptide capable of being specifically dephosphorylated by the β-isoform of calcineurin comprises a peptide having the amino acid sequence according to SEQ ID NO.: 2, wherein the S-6 position is phosphorylated, an N-terminal fluorescent TAMRA group, and a C-terminal amide group.

In embodiments of the disclosure, the reaction vessel is a well of a multi-well assay plate.

In embodiments of the disclosure, the methods may be configured for determining the efficacy of calcineurin inhibitors administered to a patient, wherein: the first test sample is obtained from a patient undergoing calcineurin inhibitor therapy following a transplant or other medical procedure requiring the same; and obtaining from the level of calcineurin activity in the test sample information as to the efficacy of drug therapy, thereby predicting the likely outcome of the patient.

Another aspect of the disclosure encompasses methods of determining the response of calcineurin of a human or animal patient to a calcineurin inhibitor, comprising: obtaining from a patient a first cell or tissue test sample and a second cell or tissue sample; determining the level of activity of calcineurin in the first test sample; determining the level of activity of calcineurin in the second test sample in the presence of a calcineurin inhibitor; and comparing the levels of calcineurin activity in the first and second samples, thereby predicting a response of the patient to a calcineurin inhibitor administered thereto.

In one embodiment of this aspect of the disclosure, the prediction of the response of a patient to an administered calcineurin inhibitor further predicts the likely outcome of a transplantation in the patient.

In one embodiment, the transplantation is a renal transplantation.

In other embodiments of the method, the step of determining the level of activity of calcineurin in the test sample comprises the steps of: contacting in a reaction mix a first test sample and a fluorescently labeled phosphorylated peptide substrate capable of being dephosphorylated by calcineurin, under conditions allowing calcineurin to dephosphorylate the fluorescently labeled phosphorylated peptide; contacting the reaction mix with a $TiO_2$ matrix, thereby partitioning fluorescently labeled phosphorylated peptide from fluorescently labeled dephosphorylated peptide; determining the fluorescence of the fluorescently labeled dephosphorylated peptide, thereby detecting calcineurin activity.

In embodiments of the methods of this aspect of the disclosure, the steps of determining the level of activity of calcineurin in the test sample may further comprise: providing a first test sample; admixing a fluorescently labeled phosphorylated peptide substrate, a reaction buffer, and a first test sample to form a first reaction mix; incubating the first reaction mix under conditions allowing calcineurin to dephosphorylate the fluorescently labeled phosphorylated peptide; providing a reaction vessel, wherein the reaction vessel is coated with a $TiO_2$ matrix, and wherein the $TiO_2$ matrix is contacted with a binding buffer; delivering the first reaction mix to the coated vessel, and incubating under conditions allowing binding of fluorescently labeled phosphorylated peptide to the $TiO_2$ matrix; transferring the first reaction mix from the coated well to a vessel containing ammonium hydroxide; and determining the amount of fluorescence emitted by fluorescently labeled phosphorylated peptide of the first reaction mix.

In embodiments of the disclosure, the assay methods may further comprise comparing the level of fluorescence emitted by the first reaction mix with the level of fluorescence emitted by at least one second test sample comprising a known amount of active calcineurin, thereby determining the amount of calcineurin in the first test sample.

In other embodiments, the assay method may be configured for high-throughput screening of a plurality of test samples by providing a plurality of test samples, thereby forming a plurality of reaction mixes.

In yet other embodiments of the disclosure, the fluorescently labeled phosphorylated peptide has an amino acid sequence selected from SEQ ID NO.: 1 and SEQ ID NO.: 2.

In one embodiment, the fluorescently labeled phosphorylated peptide is capable of distinguishing a first isoform of calcineurin from other isoforms of calcineurin.

In another embodiment the reaction vessel is a well of a multi-well assay plate.

In one embodiment of the disclosure, the fluorescently labeled phosphorylated peptide may be capable of being specifically dephosphorylated by the β-isoform of calcineurin comprises a peptide having the amino acid sequence according to SEQ ID NO.: 2, wherein the S-6 position is phosphorylated, an N-terminal fluorescent TAMRA group, and a C-terminal amide group 20.

Another aspect of the present disclosure are kits for determining the level of a phosphatase or a kinase activity in a test sample, comprising a container enclosing a fluorescently labeled peptide substrate; and instructions for the use of the peptide in determining the phosphatase or a kinase activity of a test sample.

In one embodiment of the disclosure, the kit may further comprise a reaction vessel coated with a titanium dioxide matrix.

In one embodiment of the disclosure, the peptide substrate is phosphorylated, and the instructions direct the use of the kit to determine a phosphatase activity.

In one embodiment of the disclosure, the peptide substrate is non-phosphorylated, and the instructions direct the use of the kit to determine a kinase activity.

In one embodiment of the disclosure, the kit may further comprise a reaction vessel coated with a titanium dioxide matrix.

In one embodiment of the disclosure, the coated reaction vessel is a well in a multi-well plate In one embodiment of the disclosure, the fluorescently labeled peptide has an amino acid sequence selected from the group consisting of SEQ ID NOs.: 1 and 2.

In one embodiment of the disclosure, the fluorescently labeled phosphorylated peptide having the amino acid sequence according to SEQ ID NO.: 1, is phosphorylated on the Ser-15 position, and further comprises an N-terminal fluorescein group. In one embodiment of the disclosure, the fluorescently labeled phosphorylated peptide is capable of being specifically dephosphorylated by the β-isoform of calcineurin and comprises a peptide having the amino acid sequence according to SEQ ID NO.: 2, wherein the S-6 position is phosphorylated, an N-terminal fluorescent TAMRA group, and a C-terminal amide group 20. In these embodiments the kits may include instructions for use of the kits in determining the activity of calcineurin, and optionally instructions for using the calcineurin activity to predict the outcome of administering a calicineurin inhibitor(s) to a patient.

In one embodiment of the disclosure, the kit may further comprise at least one of the group consisting of a reaction buffer; a binding buffer; ammonium hydroxide solution; a white wall reaction vessel, wherein the white wall reaction vessel is optionally a well of a multi-well plate; and at least one calcineurin activity standard solution.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

Example 1

Materials and Reagents

Recombinant calcineurin was from Calbiochem (San Diego, Calif.), and all other chemicals were obtained from Sigma (St Louis, Mo.). Titanium oxide ($TiO_2$)-coated plates were obtained from Glygen (Colombus, Mass.). The RII peptide, Fluoresceinyl-DLDVPIPGRFDRRVSVAAE, and its phosphorylated analog (Fluoresceinyl-DLDVPIPGR-FDRRVpSVAAE where pS=L-phosphoserine) were synthesized by Fmoc-based solid-phase peptide synthesis using model Liberty microwave-assisted peptide synthesizer (CEM Corporation, Matthews, N.C.). The peptides were purified to apparent homogeneity by reversed-phase HPLC and their masses were confirmed by mass spectrometry. Peptides were diluted in: Tris 50 mM, 100 mM NaCl, 0.5 mM DTT, and 0.1 mg/ml bovine serum albumen to a final concentration of 30 ng/ml. Reaction buffer consisted of 0.1 mg/ml BSA, 35 mM Tris pH 7.5, 25 mM NaCl, 2.0 mM $MgCl_2$ >270 \M DTT, 500 \M EDTA, 419 nM okadaic acid (in 0.63% ethanol), 25 mM $CaCl_2$ or 500 uM EGTA. $TiO_2$ plates were pre-incubated with a binding buffer consisting of 0.1% acetic acid in 10% acetonitrile.

Example 2

20 μl diluted peptide substrate, 20 μl of reaction buffer, and 20 μl of sample were loaded into individual wells of a 96-well plate and incubated at 30° C. for 10 minutes. During the reaction time, a 96-well plate with $TiO_2$ coated wells was prepared by adding 50 μl binding buffer (0.1% acetic acid in 10% acetonitrile) per well. After the incubation period, reactions were transferred into prepared $TiO_2$-coated wells following by gentle shaking for 5 minutes. The contents of each well were then removed to a white 96-well plate preloaded with 20 μl of 3N ammonium hydroxide. The amount of fluorescent label that did not bind to the $TiO_2$ matrix was quantified by fluorimetry at 485 nm excitation 528 nm emission.

Example 3

Experimental Models

Primary mouse renal fibroblasts were obtained from minced kidneys and propagated in culture using RPMI supplemented with 5% serum and pen/strep antibiotics. Lysates were prepared using a hypotonic lysis buffer (see Gooch et al., *J. Biol. Chem.* 276 (2001) 42492-500; Gooch et al., J. Biol. Chem. 279 (2004) 15561-70; incorporated herein by reference in their entireties). Where indicated, wild type mice were treated by sub-cutaneous injection with either vehicle alone (10% ethanol in Ringer's lactate solution) or with 10 mg/kg body weight cyclosporin A daily for 3 days. Organs were harvested and calcineurin activity determined as described by Gooch et al., Am. J. Pathology. 165 (2004) 1755-1765, incorporated herein by reference in its entirety.

Example 4

Mass Spectrometry

The system used for the analysis was an Ultimate capillary HPLC system (LC Packings) with a FAMOS autosampler. An 0.5×150 mm C18SB-300 Zorbax (Agilent, Technologies, Palo Alto, Calif.) reversed-phase column was used as the analytical column. The LC eluent was directly sprayed into the 4000QTRAP mass spectrometer using a TurboV electrospray ion source (Applied Biosystems, Foster City, Calif.). Elution from the column was accomplished with an acetonitrile gradient from 2% to 80% with 0.1% formic acid as a counter ion for HPLC. The flow rate was set at 15∥l/min. The total LC run time was 60 minutes including equilibration. The 4000Qtrap was operated both in the information dependent acquisition (IDA) mode and straight MS mode. In IDA, for each cycle, a single MS spectrum was acquired followed by up to two MS/MS spectra based upon observed ions in the MS spectrum. The MS spectrum was acquired over the m/z range of 350 to 1,350. Each MS/MS spectrum was acquired over the m/z range of 50 to 1,350. Precursors were determined by each cycle's MS spectrum from the m/z range of 375 to 1,100. Straight MS was performed over the m/z range of 350 to 1,350. For each sample, extracted ion chromatograms (XIC) were generated for the phosphorylated and non-phosphorylated versions of the RII peptide. The width used for the XIC was 1 Dalton. Based on the areas of the peaks from each XIC, the relative quantity of phosphorylated to non-phosphorylated peptide was determined.

Example 5

T Cell Isolation and Treatment 40 mLs of heparinized blood was collected from the study participants. T cells were then isolated using the Prepacyte SC reagent (BioE WBP2000 St. Paul Minn.) antibody negative selection and Vitalyse (BioE K1-135) treated to eliminate remaining erythrocytes. Cells were pelleted by centrifugation, washed with 1× phosphate-buffered saline, and resuspended in RPMI 1640 containing penicillin/streptomycin antibiotics, 10% fetal calf serum, 2 mM l-glutamine, 25 mM glucose, and 1 mM sodium pyruvate. Resulting cells were identified by flow cytometry and found to be 98-99% CD3+, CD4+. For treatment with inhibitors, isolated T-cells were separated into equal aliquots and preincubated for 15 minutes with FK506 (5 ng/ml), cyclosporin (5 µg/ml) or DMSO then, if stimulated, treated for 30 minutes with anti-CD3/CD28 antibodies (10 µg/ml each) (BD Biosciences, San Jose, Calif.).

Example 6

Non Fluorescent Calcineurin Assay

Calcineurin activity was determined using an in vitro assay as described in Fruman et al., *Methods in Enzymology* 9, 146-154 (1996) and Lea et al., *J Am Soc Nephrol* 13, 1750-1756 (2002), both of which are incorporated herein by reference in their entireties. Following treatment, isolated lymphocytes were pelleted and then re-suspended in calcineurin buffer (100 µM Tris, 250 µM KCl, 10 mg/ml BSA, 5 mg/ml DTT, pH 7.5). Cells were then lysed by three cycles of freeze-thawing in liquid nitrogen and a 37° C. water bath. The concentration of harvested proteins was determined by the BCA method (Pierce Biotechnology, Rockford, Ill.) and then 10 µg of sample was incubated with equal volumes of calcineurin reaction buffer (100 nM calmodulin, 0.1 mM CaCl, 25 µgs calyculin, 3 µg cold RII peptide) and 3 µg $\gamma^{32}$P[ATP]-labeled RII peptide substrate.

The reaction was allowed to proceed for 10 minutes, and then 10 mgs/ml charcoal/TCA solution was added to each sample to stop the reaction. Finally, samples were passed through millipore filtration buckets, scintillation fluid added, and the amount of released phosphates read in an automated counter. Reactions were performed in triplicate and final data for subjects were calculated as the mean of triplicate samples minus control reactions to normalize for background.

Example 7

Cytokine Array

Cytokine arrays were carried out according to the manufacturer's instructions (Panomics Cytokine Array, Fremont Calif.). Briefly, array membranes were incubated for 1 hour in 1×blocking buffer, and then incubated with the biotin-conjugated anti-cytokine mix for 2 hours. The membranes were then incubated with streptavidin/horseradish peroxidase-conjugated secondary antibody at room temperature for 30 minutes. Finally, following treatment with detection buffer for 5 minutes, membranes were developed with ECL, visualized by radiography, and quantitated by densitometry. Each duplicate spot of cytokine was normalized to internal controls provided by the manufacturer. Data was obtained as the fold difference in each cytokine compared to the internal controls.

Example 8

Statistics

All statistical calculations were carried our using GraphPad Prism scientific graphing and analysis software. Paired T tests and repeated measure analysis of variance (ANOVA) were used as indicated to compare multiple treatments of individual samples. For comparison of 3 or more groups, ANOVA (or repeated measure ANOVA, as appropriate) was used in conjunction with Tukey's post-test. Cytokine array data were analyzed by linear regression. All results were considered significant if $p<0.05$.

Example 9

Calcineurin is the target of immunosuppressive drugs but very little is known about how calcineurin activity changes in T cells of transplant patients. To begin, a random group of control subjects (see Methods) was recruited. Gender, age, height, weight, and racial identification were self-reported by the volunteers. 50% were male, 50% female, the average age was 35.3, and the average body mass index was 27.5. 5% were Asian, 45% Caucasian, and 50% African American. Blood was drawn from 82 subjects and T cells were isolated by negative antibody selection using Prepacyte SC reagent. Calcineurin activity was determined using an in vitro assay as previously described by Fruman et al., *Methods in Enzymology* 9, 146-154 (1996), and Gooch et al., *J. Biol. Chem.* 279, 15561-70 (2004), incorporated herein by reference in their entireties.

T cell isolates were stimulated for 15 minutes with multiple agents including calcium ionophore, phorbal myristate acid (PMA), and anti-CD3/CD28 antibodies. CD3/CD28 co-stimulation resulted in the most consistent and robust stimulation of calcineurin activity. When compared with basal, unstimulated levels, CD3/CD28 co-stimulation resulted in a significant increase in calcineurin activity (paired T-test), as shown in FIG. 5A. Next, T cells were pre-treated for 30 minutes with CsA (5 mg/ml) or FK506 (5 ng/ml) and then CD3/CD28-mediated stimulation was measured. Both CsA and FK506 significantly reduced CD3/CD28-mediated calcineurin activity (ANOVA, Tukey's posts-test), as shown in FIG. 5B.

Thirty-nine patients who were receiving outpatient care and who had undergone kidney transplant were recruited for the study. Demographic data (Table 1) was obtained as well as post-transplant characteristics, as shown in Table 2.

TABLE 1

| | | Study group characteristics | | | | | | |
|---|---|---|---|---|---|---|---|---|
| | | Gender | | Race | | | | |
| Groups | N | Male | female | Caucasian | AA | Asian | Hispanic | Age | BMI |
| Control | 82 | 50.0% | 50.0% | 50.0% | 45.1% | 4.9% | 0 | 35.3 | 27.5 |
| Transplan | 39 | 56.4% | 43.6% | 57.6% | 44.1% | 1.7% | 1.7% | 47.5 | 28.6 |

TABLE 2

Transplant group characteristics

| Transplant group: | All (n = 39) | Caucasians (n = 19) | African-American (n = 18) |
|---|---|---|---|
| Diagnoses | | | |
| Diabetes/Hypertension | 51.3% | 47.4% | 61.1% |
| PCKD | 18.0% | 26.3% | 11.1% |
| Glomerular disease | 18.0% | 15.8% | 11.1% |
| Other | 12.8% | 10.5% | 16.7% |
| Type of Transplant | | | |
| Living, related | 21.1% | 36.8% | 5.6% |
| Living, unrelated | 13.2% | 15.8% | 11.1% |
| Deceased | 65.8% | 47.4% | 83.3% |
| Time Since Transplant | | | |
| mean | 22 +/− 6 | 19 +/− 8 | 25 +/− 10 |
| range | 1-175 | 1-133 | 1-167 |
| <1 yr | 61% | 74% | 67% |
| >1 yr | 31% | 26% | 33% |

56% of the group was male, while 44% was female. The average age and BMI of the post-transplant patients was slightly higher than the control group at 47.5 years and 28.6, respectively. 2 patients were of Asian descent, 18 were Caucasian (CC), and 19 self-reported as African American (AA), a racial distribution that was similar to the control group. All patients were on standard post-transplant immune suppression, which included calcineurin inhibitors (31 received FK506, while 8 were treated with CsA).

Consistent with previous reports, AA patients were more likely to have been diagnosed with hypertension and/or diabetes than CC patients, and were more likely to have received kidneys from deceased donors rather than living donors. However, other characteristics including kidney function were comparable between CC and AA patients (MDRD estimated GFR was 56.9 for CC and 56.4 for AA subjects), Basal and anti-CD3/CD28-stimulated calcineurin activity was measured in T cells isolated from transplant patients, as shown in FIG. 5C. Unlike the control group, CD3/CD28 antibodies failed to induce a significant increase in calcineurin activity (paired T-test). The mean percent increase in non-transplant control subjects' calcineurin activity was 41% compared to only 8% for transplant patients, a significant difference ($p<0.01$) (FIG. 5D).

Example 10

While calcineurin inhibitors have been instrumental in improving short-term graft survival, a variety of factors including race have been demonstrated to effect long-term outcomes. Calcineurin activity of CC and AA transplant patients was therefore analyzed to determine if there were differences in basal activity or anti-CD3/CD28 co-stimulation. CC transplant patients had significantly higher basal levels of calcineurin activity compared to both controls and to AA transplant patients (ANOVA, Tukey's post-test), as shown in FIG. 6A. In contrast, basal calcineurin activity in the AA group was not different from that of controls. Stimulation of calcineurin activity was also determined for CC and AA transplant patients. There was no significant increase in calcineurin activity in response to anti-CD3/CD28 co-stimulation in T cells from CC patients. In contrast, stimulation of calcineurin activity in AA transplant patients was a mean of 36%), a level not significantly difference from control subjects (ANOVA, Tukey's post-test) (FIG. 6B). Trough blood levels of FK506 for both CC and AA transplant patients were obtained at the time of T cell isolation. There was no significant difference between the mean trough FK506 blood level of 11.4+/−0.7 for CCs and 12.0+/−0.9 for AAs or between CsA levels of 227+/−99.9 for CC and 131+/−31.4 for AA patients.

To further investigate the relationship between calcineurin activity and race, control subjects were analyzed by self-reported racial group. Four volunteers were identified as Asian, 41 as Caucasian and 37 as African American, a distribution that was comparable to the transplant cohort. Anti-CD3/CD28 co-stimulation resulted in a significant increase in calcineurin activity in both CC and AA controls. The percent increases were not different between the two groups, nor were the basal, unstimulated levels of calcineurin activity. Stimulation of calcineurin activity by anti-CD3/CD28 in CC controls was inhibited by both CsA and FK506 (FIG. 6C). However, neither CsA nor FK506 significantly reduced calcineurin activity in AA volunteers (FIG. 6D).

Example 11

Since factors that may modify long-term graft survival such as cytokine expression are also known to vary by race, it was possible that changes in calcineurin activity correlate with changes in cytokine expression. Cytokine production by isolated T cells from a subset of patients (N=6; 3 CC and 3 AA) was examined using a Panomics cytokine array. Results of cytokine levels were compared by linear regression analyses with both basal and fold stimulation of calcineurin in the same patients. FIGS. 7A and 7B show that IL-4 and IL-10 were inversely correlated with changes in basal calcineurin. Higher levels of cytokine expression correlate with lower basal calcineurin activity. In contrast, FIGS. 7C and 7D show that IL-2 and TGFβ were positively correlated with changes in anti-CD3/CD28-stimulation of calcineurin. Higher cytokine expression is correlated with higher levels of calcineurin stimulation. IL-3 correlated with both changes in basal and changes in fold stimulation while other cytokines including IFNγ, TNFα, and IL-6 showed a small or no association with calcineurin and are described in Table 2.

TABLE 2

Correlation of basal and stimulated calcineurin with cytokine regulation

| T cell cytokine production | Calcineurin (basal) | | Calcineurin (fold increase) | |
|---|---|---|---|---|
| | $R^2$ | P value | $R^2$ | P value |
| TGFP | .018 | 100 | .637 | .057 |
| IFNy | .419 | .165 | .138 | .468 |
| TNFa | .057 | .076 | .145 | .457 |
| IL-2 | .263 | .298 | .807 | .015* |
| IL-3 | .883 | .005* | .785 | .019* |
| IL-4 | .639 | .056 | .383 | .190 |
| IL-6 | .502 | .115 | .187 | .392 |
| IL-10 | .660 | .048* | .311 | .250 |

FIGS. 7A-7D, and Table 2 demonstrate that while increased T cell expression of some cytokines are associated with lower basal levels of calcineurin, other cytokines including TGF|| appear to be regulated concomitantly with stimulated calcineurin activity.

Example 12

Figure 8A:
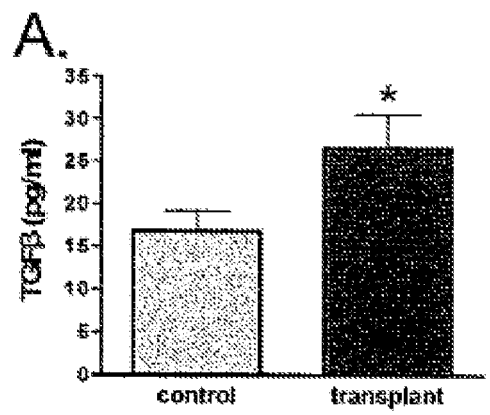
Figure 8B:
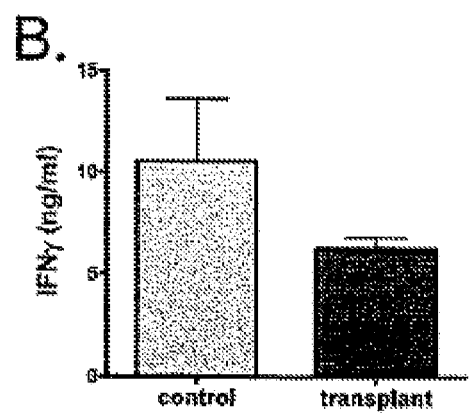
Figure 8C:
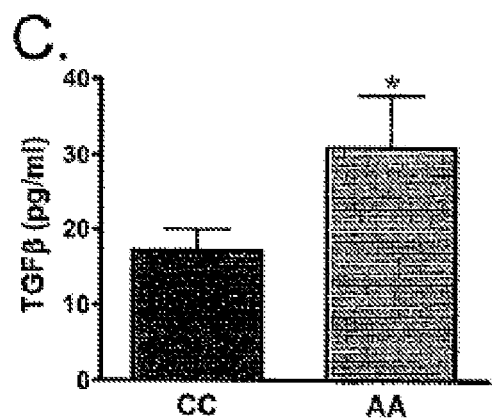
Figure 8D:
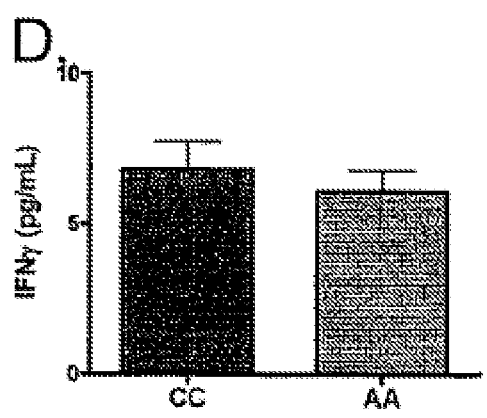

FIGS. 8A-8D show that in the control and transplant cohorts recruited for this study, serum TGFβ levels were higher in transplant patients compared to control subjects (FIG. 8A). The mean levels of IFNγ were also lower in transplant patients, although the change did not reach significance (FIG. 8B). Similarly, AA transplant patients had significantly higher levels of serum TGFβ compared to CC transplant patients (FIG. 8C), while there was no difference in the levels serum IFNγ (FIG. 8D).

TABLE 4

Multivariate Analysis by control/transplant group

|  | CI dose | Race | Gender | Age | BMI |
|---|---|---|---|---|---|
| Control Group |  |  |  |  |  |
| Basal activity | n/a | ns | ns | ns*[1] | ns |
| Stimulation | n/a | ns | p < 0.05 | ns | ns*[2] |
| Sensitivity to calcineurin inhibitors | n/a | p < 0.05 | ns | ns | ns |
| Transplant Group |  |  |  |  |  |
| Basal activity | ns | p < 0.05 | ns | ns | p < 0.05*[4] |
| Stimulation | ns | p < 0.01 | p < 0.05 | ns*[3] | ns |

*[1] trend for CC(p < .1)
*[2] p < 0.05 for CC
*[3] p < 0.01 for CC
*[4] p < 0.05 for CC, ns for AA

We claim:

1. A method of determining calcineurin activity comprising the steps of:
   i) contacting in a reaction mix a first test sample and a fluorescently-labeled phosphorylated peptide substrate capable of being dephosphorylated by calcineurin, under conditions such that calcineurin dephosphorylates the fluorescently-labeled phosphorylated peptide; and
   ii) contacting the reaction mix with a TiO2 matrix, thereby partitioning fluorescently-labeled phosphorylated peptide from fluorescently-labeled non-phosphorylated peptide providing a partition with fluorescently-labeled non-phosphorylated peptide; and
   iii) determining calcineurin activity wherein measuring an amount of fluorescence emitted by the partition with fluorescently-labeled non-phosphorylated peptide is an indication of calcineurin activity.

2. The method of claim 1, wherein the fluorescently labeled phosphorylated peptide has an amino acid sequence selected from SEQ ID NO.: 1 and SEQ ID NO.: 2.

3. The method of claim 1, wherein the fluorescently labeled phosphorylated peptide is capable of distinguishing a first isoform of calcineurin from a second isoform.

4. The method of claim 2, wherein the fluorescently labeled phosphorylated peptide has the amino acid sequence according to SEQ ID NO.: 1, is phosphorylated on the Ser-15 position, and further comprises an N-terminal fluorescein group.

5. The method of claim 2, wherein the fluorescently labeled phosphorylated peptide has the amino acid sequence according to SEQ ID NO.: 2, wherein the S-6 position is phosphorylated, an N-terminal fluorescent TAMRA group, and a C-terminal amide group.

6. The method of claim 1, further comprising the step of comparing the amount of fluorescence emitted by the partition with fluorescently-labeled non-phosphorylated peptide with a fluorescence emitted by at least one second test sample comprising a known amount of active calcineurin.

7. The method of claim 1, further comprising comparing the amount of fluorescence emitted by the partition with fluorescently-labeled non-phosphorylated peptide with a fluorescence emitted by at least one second test sample, wherein the second test sample includes a calcineurin inhibitor.

8. The method of claim 1, wherein the method is repeated on a plurality of test samples.

9. The method of claim 8 wherein test samples are in a multi-well assay plate.

10. The method of claim 1, the test sample is obtained from a patient, wherein the patient is in need of a transplant or has received a transplant.

\* \* \* \* \*